Figure 1:
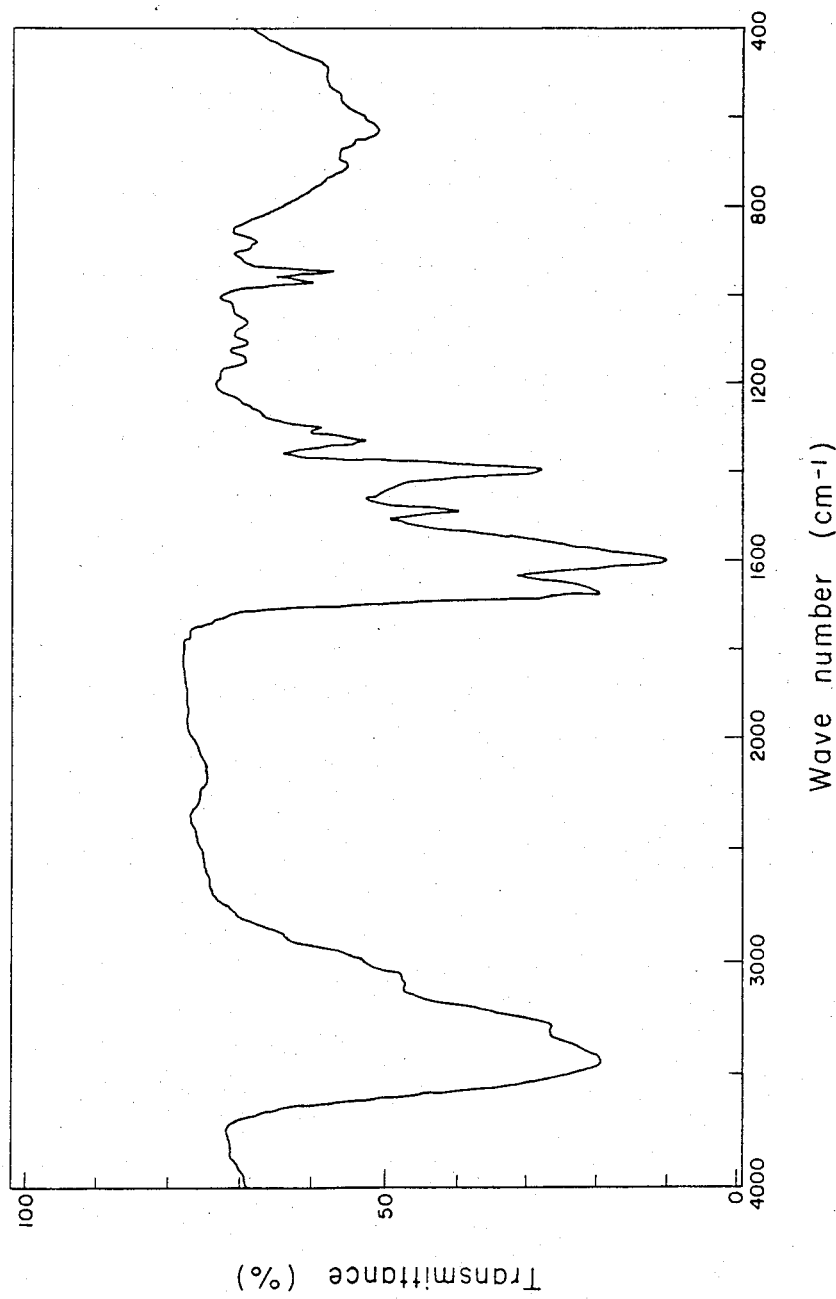

United States Patent [19]

Kanamaru et al.

[11] Patent Number: 4,521,432

[45] Date of Patent: Jun. 4, 1985

[54] PHYSIOLOGICALLY ACTIVE SUBSTANCE FA-5859, ITS DERIVATIVE, THEIR PRODUCTION AND USE

[75] Inventors: Tsuneo Kanamaru, Takatsuki; Susumu Shinagawa, Higashiosaka; Mitsuko Asai, Takatsuki, all of Japan

[73] Assignee: Takeda Chemical Industries, Ltd., Osaka, Japan

[21] Appl. No.: 442,368

[22] Filed: Nov. 17, 1982

[30] Foreign Application Priority Data

Nov. 26, 1981 [JP] Japan .................. PCT/JP81/00355
Jul. 28, 1982 [JP] Japan .................. PCT/JP82/00291
Oct. 15, 1982 [JP] Japan .................. PCT/JP82/00409

[51] Int. Cl.$^3$ ............... C07C 87/30; A61K 31/24; A61K 31/195
[52] U.S. Cl. ................ 514/556; 260/501.13; 514/866
[58] Field of Search ............. 260/501.13; 424/316

[56] References Cited

FOREIGN PATENT DOCUMENTS 1442318 3/1966 France ........................ 260/501.13
1093937 12/1967 United Kingdom ........... 260/501.13

*Primary Examiner*—Richard Raymond
*Assistant Examiner*—Raymond Covington
*Attorney, Agent, or Firm*—Wegner & Bretschneider

[57] ABSTRACT

Physiologically active substance FA-5859 and its deacetyl compound represented by the formula:

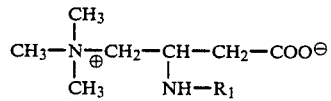

wherein $R_1$ is a hydrogen atom or an acetyl group, are produced by a cultivation of a microorganism of the genus Emericella or Aspergillus (compound wherein $R_1$ is an acetyl group) or by a method of chemical synthesis (compound wherein $R_1$ is a hydrogen atom or an acetyl group).

Said compounds or a salt thereof have excellent fatty acid degradation inhibiting activity and is useful as an antidiabetic agent in mammalian animals or as a biochemical reagent for studies on fatty acid metabolism.

4 Claims, 2 Drawing Figures

PHYSIOLOGICALLY ACTIVE SUBSTANCE FA-5859, ITS DERIVATIVE, THEIR PRODUCTION AND USE

The present invention relates to physiologically active substance FA-5859, its derivatives their production and use.

Among the hitherto-known compounds having fatty acid degradation inhibiting activity are 4-pentenoic acid [P.C. Holland et al., Biochemical Journal 136, 157 and 173, 1973; H. S. A. Sherratt et al., Biochemical Pharmacology 25, 743, 1976], hypoglycin [H. S. A. Sherratt et al., Biochemical Pharmacology 25, 743, 1976], decanoyl-(+)-carnitine and 2-bromopalmitoyl CoA [I.B. Fritz et al., Proceedings of the National Academy of Sciences, U.S.A. 54, 1226, 1965], but none of them have been used clinically because of toxicity and adverse reactions. Methyl-2-tetradecyl glycidate and 2-tetradecyl glycidate [G. F. Tutwiller et al., Diabetes 28, 242, 1979 and Methods in Enzymology 72, 533, 1981] are known to have fatty acid degradation inhibiting activity and show a hypoglycemic action with oral administration.

There has for sometime been a demand for a more effective antidiabetic drug having a new mode of action for the treatment of diabetes and its complications, the incidence of which has been on the steady increase. Thus, in diabetes, as an insulin deficiency promotes a liberation of fatty acids in the adipose tissue, there occurs an increased supply of fatty acids to the liver and as the decomposition of fatty acids is concurrently promoted, the production of ketone compounds is stimulated, leading to the so-called ketonemia. In the extrahepatic tissues, the utilization of glucose is poor and the ketone compounds so produced are used as energy sources. Therefore, it is expected that if the decomposition of fatty acids is inhibited, the production of ketone compounds will be attenuated and, consequently, the utilization of glucose be promoted so that blood sugar levels are ultimately decreased. In other words, a specific inhibitor of fatty acid degradation would be of value as a new antidiabetic drug relying on a new mechanism of action. In view of these background facts, the present inventors made an extensive screening study for the development of a new antidiabetic and discovered a substance capable of inhibiting the decomposition of fatty acids in culture broths of microorganisms belonging to the genus Emericella or the genus Aspergillus. The present inventors isolated the substance and found that it is a novel substance and that it has an excellent activity to inhibit degradation of fatty acids. Accordingly, the substance was named "physiologically active substance FA-5859".

The present inventors have assumed that the chemical structure of physiologically active substance FA-5859 is the following:

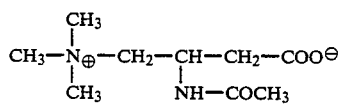

The present inventors then conducted an intensive study to develop derivatives of the substance and found that the deacetyl derivative obtainable by hydrolysis of FA-5859 is a novel substance having a remarkable fatty acid degradation inhibiting activity. This new derivative was named "physiologically active substance deacetyl-FA-5859".

As a result of further intensive research by the present inventors in search of methods for the chemical synthesis of the physiologically active substance deacetyl-FA-5859 and the physiologically active substance FA-5859, it has been found that compounds of the general formula [1]:

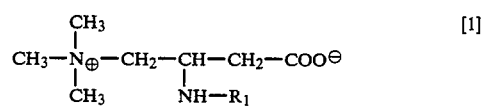

wherein $R_1$ is a hydrogen atom or an acetyl group, or salts thereof can advantageously be produced either by subjecting a compound of the general formula [2]:

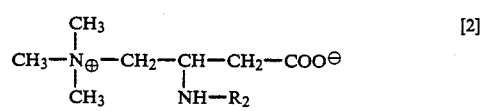

wherein $R_2$ is a protective group other than an acetyl group, or a salt thereof to elimination reaction of the protective group, if necessary followed by acetylation, or by subjecting a compound of the formula [3]:

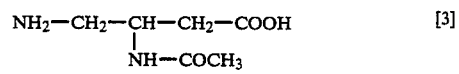

or a salt thereof to trimethylation, if necessary followed by hydrolysis.

The present invention is predicated on the above findings and further studies.

Thus, the present invention relates to (1) a compound of the formula [1]:

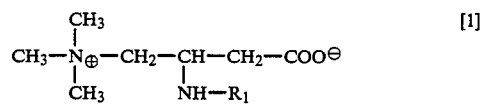

wherein $R_1$ is a hydrogen atom or an acetyl group, or a salt thereof, (2) a method of producing physiologically active substance FA-5859 characterized by cultivating a physiologically active substance FA-5859-producing microorganism belonging to the genus Emericella or the genus Aspergillus in a culture medium to cause the microorganism to elaborate and accumulate physiologically active substance FA-5859 in the cultured broth and recovering the same from the broth, (3) a method of producing a compound of the formula [1']:

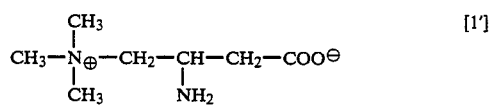

or a salt thereof characterized by hydrolyzing a compound of the formula [3]:

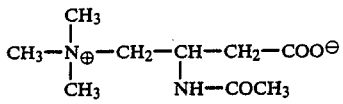

or a salt thereof, (4) a method of producing the compound [1] or a salt thereof, which comprises subjecting a compound of the general formula [2]:

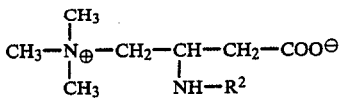

wherein $R_2$ is a protective group other than an acetyl group, or a salt thereof to elimination reaction of the protective group, if necessary followed by acetylation, (5) a method of producing the compound [1] or salts thereof, which comprises subjecting a compound of the formula [3]:

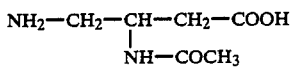

or a salt thereof to trimethylation, if necessary followed by hydrolysis, and (6) an antidiabetic agent which contains a compound of the formula [1] or a salt thereof.

In this specification, the compound of formula [1] wherein $R_1$ is a hydrogen atom is sometimes called "physiologically active substance deacetyl FA-5859" or simply "deacetyl-FA-5859", and the compound of formula [1] wherein $R_1$ is an acetyl group is sometimes referred to as "physiologically active substance FA-5859" or simply "FA-5859".

In the above formula [2], the protective group other than an acetyl group as represented by $R_2$ includes, among others, tert-butyloxycarbonyl, benzyloxycarbonyl, p-methoxybenzyloxycarbonyl or p-nitrobenzyloxycarbonyl.

FA-5859 (free form) of the present invention has the following physico-chemical properties.

(a) Elemental analysis (%): (After drying under reduced pressure over phosphorus pentoxide at 60° C. for 10 hours)
 C: 51.16±2.0
 H: 9.06±1.0
 N: 13.26±1.0
(b) Molecular weight: $2.4-3.3 \times 10^2 (H_2O)$ (by VPO method)
(c) Specific rotation: $[\alpha]_D^{23} -17.4° \pm 3°$ (c=1, $H_2O$)
(d) Ultraviolet absorption spectrum: no characteristic absorption
(e) Infrared absorption spectrum [dominant absorptions (wave-numbers), KBr disc]: 1660, 1590, 1485, 1400, 1325, 1295, 970, 945 ($cm^{-1}$)
(f) Solubility:
 Insoluble: Petroleum ether, hexane, diethyl ether, benzene, ethyl acetate, chloroform
 Hardly soluble: Pyridine, acetone, dimethyl sulfoxide, dimethylformamide
 Soluble: Ethanol, methanol
 Readily soluble: Water
(g) Color reactions:
 Positve: Iodine reaction
 Negative: Greig-Leaback, ninhydrin, Sakaguchi, Molisch, Ehrlich reactions
(h) Basic, acid or neutral: Amphoteric
(i) Color or the substance: Colorless FA-5859 can be produced by cultivating a physiologically active substance FA-5859-producing microorganism belonging to the genus Emericella or the genus Aspergillus in a culture medium to cause the microorganism to elaborate and accumulate FA-5859 in the cultured broth and recovering the same from the broth.

The microorganism which can be used in the above-mentioned fermentation process may be any strain of microorganism, when it belongs to the genus Emericella or the genus Aspergillus and is able to elaborate said physiologically active substance FA-5859. Examples of such microorganism include *Emericella quadrilineata, Emericella nidulans* var. *acristata, Emericella cleistominuta, Emericella nidulans* var. *nidulans, Emericella nidulans* var. *lata, Emericella rugulosa, Emericella nidulans, Emericella sublata,* and the species of Aspergillus to which Aspergillus sp. No. 3704 belongs. More particularly, there can be employed *Emericella quadrilineata* IFO 5859, *Emericella quadrilineata* IFO 30911, *Emericella quadrilineata* IFO 30912, *Emericella quadrilineata* IFO 30850, *Emericella quadrilineata* IFO 30851, *Emericella nidulans* var. *acristata* IFO 30063, *Emericella nidulans* var. *acristata* IFO 30844, *Emericella cleistominuta* IFO 30839, *Emericella nidulans* var. *nidulans* IFO 30872, *Emericella nidulans* var. *lata* IFO 30847, *Emericella rugulosa* IFO 8626, *Emericella rugulosa* IFO 8629, *Emericella rugulosa* IFO 30913, *Emericella rugulosa* IFO 30852, *Emericella rugulosa* IFO 30853, *Emericella idnulans* IFO 5719, *Emericella nidulans* IFO 7077, *Emericella indulans* IFO 30062, *Emericella sublata* IFO 30906, Aspergillus sp. No. 3704, etc.

Among the above-mentioned strains, the strains of IFO 5859, IFO 30063, IFO 8626, IFO 8629, IFO 5719, IFO 7077 and IFO 30062 have been deposited at Institute for Fermentation, Osaka (17-85, Juso-Honmachi 2-chome, Yodogawa-ku, Osaka 532, Japan), and listed on Institute for Fermentation, Osaka, List of Cultures, 1978, Sixth Edition.

The strains of IFO 30911, IFO 30912, IFO 30850, IFO 30851, IFO 30844, IFO 30839, IFO 30872, IFO 30847, IFO 30913, IFO 30852, IFO 30853 and IFO 30906 have been deposited in Institute for Fermentation, Osaka and listed on Institute for Fermentation, Osaka, Research Communications, No. 10, 1981.

The dates of deposit of the above-mentioned strains at Institute for Fermentation, Osaka are as follows.

| Microorganism | Date of deposit |
| --- | --- |
| IFO 5859 | September 14, 1954 |
| IFO 30911 | January 10, 1980 |
| IFO 30912 | January 10, 1980 |
| IFO 30850 | July 18, 1979 |
| IFO 30851 | July 18, 1979 |
| IFO 30063 | August 8, 1975 |
| IFO 30844 | July 18, 1979 |
| IFO 30839 | July 18, 1979 |
| IFO 30872 | November 9, 1979 |
| IFO 30847 | July 18, 1979 |
| IFO 8626 | August 29, 1966 |
| IFO 8629 | August 2, 1966 |
| IFO 30913 | January 10, 1980 |
| IFO 30852 | July 18, 1979 |
| IFO 30853 | July 18, 1979 |
| IFO 5719 | April 18, 1953 |
| IFO 7077 | February 3, 1962 |
| IFO 30062 | August 8, 1975 |

| -continued | |
|---|---|
| Microorganism | Date of deposit |
| IFO 30906 | January 10, 1980 |

Referring to the above-mentioned microorganisms., the microbiological characteristics of *Emericella quadrilineata* are the same as those described in Transactions of the Mycological Society of Japan, Vol. 20, No. 4, 481 (1979). The microbiological characteristics of *Emericella nidulans* var. *acristata* are as described in Reports of The Tottori Mycological Institute No. 12, 171 (1975). The microbiological characteristics of *Emericella cleistominuta* are as described in Transactions of The British Mycological Society, Vol. 52, No. 2, 331 (1969). The microbiological characteristics of *Emericella nidulans* var. *nidulans* are as described in Korean Journal of Microbiology, Vol. 18, No. 2, 104 (1980). The microbiological characteristics of *Emericella nidulans* var. *lata* are as described in K. B. Raper, B. I. Fennel: The Genus of Aspergillus, page 500, The Williams & Wilkins Company, Baltimore, 1965. The microbiological characteristics of *Emericells rugulosa* are as described in Transactions of The Mycological Society of Japan, Vol. 20, No. 4, 481 (1979). The microbiological characteristics of *Emericella nidulans* are as described in K. B. Raper, B. I. Frennel: The Genus Aspergillus, page 495, The Williams & Wilkins Company, Baltimore, 1965. The microbiological characteristics of *Emericella sublata* are as described in Transactions of The Mycological Society of Japan, Vol. 20, No. 4, 481 (1979).

Aspergillus sp. No. 3704 is a fungus isolated from the field soil sample obtained at Daiwa-cho, Kawanishi, Hyogo Prefecture, Japan and has the following microbiological characteristics.

Cultural characteristics:
(1) Czapek agar
Slow growth; colonies after 2 weeks at 24° C. are 1.4 to 2.0 cm in diameter. A tough mycelial felt with a slightly raised center, and with an irregular and deeply submerged margin. The surface growth shows a network of ascending hyphae. The color of the growth was pale bluish-green with a tinge of yellow, and became a pale brown shade with aging. Conidial heads are few. Reverse color is pale brown to brown. As the culture ages, a pale brown soluble pigment is produced.

(2) Malt extract-agar
Good growth; colonies after 2 weeks at 24° C. are 4.0 to 5.0 cm in diameter. Plane with a thin, slightly tufted margin. Aerial growth is sparse. Conidial heads are abundant, assuming a yellow-green color with a tinge of gray.
Reverse color is pale brown to yellowish brown.
No production of soluble pigments.

Morphology:
Conidial heads: Though not uniform in size, conidial heads are 75 to 100$\mu$ long and 20 to 40$\lambda$ in diameter; radiate when young but gradually becoming a pseudocylindrical shape.
Conidiophores: 40 to 60$\mu$ long and 2.0 to 4.5$\lambda$ in diameter, with a smooth wall, colorless and slightly curved.
Vesicles: Flask-shaped, with a flat tip, 4.5 to 7.5$\mu$ in diameter.
Metulae: Cylindrical, 4.5 to 6.2×2.4 to 3.4$\mu$.
Phialide: Club-shaped, 4.5 to 6.5×2.0 to 3.0$\mu$.
Conidia: Spherical to ellipsoidal, dark green, 2.5 to 3.5$\mu$ in diameter.

Referring the above characteristics to the characteristics of fungi of the genus Aspergillus as described in Shunichi Udagawa et al.: "Kinrui Zukan" (Plates of Funji) (Kodansha, Japan, 1978), p. 1006 shows clearly that the above strain of microorganism belongs to the genus Aspergillus.

The above Aspergillus sp. No. 3704 was deposited and has been stored at Institute for Fermentation, Osaka on Nov. 6, 1981 under the accession number of IFO 31171.

The microorganism Aspergillus sp. No. 3704, which was deposited on Nov. 18, 1981 at Fermentation Research Institute, Agency of Industrial Science and Technology, Ministry of International Trade and Industry, Japan (FRI, 1-3, Higashi 1-chome, Yatabe-machi, Tsukuba-gun, Ibaraki Prefecture 305, Japan) under the accession number of FERM P-6224, the deposit being converted to a deposit under the Budapest Treaty, has been stored at FRI under the accession number of FERM BP-185.

As to the genus Emericella, since it is a taxonomic grouping of Aspergillus strains with established complete life cycles, it goes without saying that any strain that is able to elaborate FA-5859 can be utilized irrespective of sexual generation or asexual generation.

As it is true of microorganisms in general, microorganisms of the genus Emericella and of the genus Aspergillus are liable to undergo mutation whether spontaneously or under the influence of a mutagen. Thus, any and all mutants that are obtainable by irradiation with X-rays, gamma rays, ultraviolet light, etc., monospore separation, treatment with certain reagents or cultivation in media containing such reagents, or other mutagenic treatments, as well as those spontaneous mutants that may be available, can be successfully employed in the production of FA-5859 when they are still capable of elaborating FA-5859.

The medium used for the production of FA-5859 may be liquid or solid, insofar as it contains nutrients available to the strain employed, although a liquid medium is suited for mass production. In the medium are incorporated suitable proportions of assimilable carbon sources, digestable nitrogen sources, inorganic substances and trace nutrients. The carbon sources may for example be glucose, lactose, sucrose, maltose, dextrin, starch, glycerin, mannitol, sorbitol and oils and fats (e.g. soybean oil, olive oil, bran oil, sesame oil, lard oil, chicken oil, etc.), fatty acids (e.g. lauric acid, myristic acid, palmitic acid, stearic acid, oleic acid, etc.). The nitrogen sources may for example be meat extract, yeast extract, dried yeast, soybean flour, corn steep liquor, peptone, cottonseed flour, spent molasses, urea, ammonium salts (e.g. ammonium sulfate, ammonium chloride, ammonium nitrate, ammonium acetate, etc.) and so on. In addition, salts including those of sodium, potassium, calcium, magnesium, etc., metal salts such as those of iron, manganese, zinc, cobalt, nickel, etc., salts of phosphoric acid, boric acid, etc., and salts of organic acids such as acetic acid, propionic acid, etc. are also used as necessary. It is, of course, possible to add amino acids (e.g. glutamic acid, aspartic acid, alanine, lysine, valine, methionine, proline, etc.), peptides (e.g. dipeptides, tripeptides, etc.), vitamins (e.g. $B_1$, $B_2$, nicotinic acid, $B_{12}$, C, etc.), nucleic acids (e.g. purine and pyrimidine and their derivatives) and others. Of course, for the purpose of controlling the pH of the medium, an organic or inorganic acid, an alkali, a buffer solution or the like may be added. For defoaming purposes, an oil, a surfactant or the like may also be added to the medium.

The cultural methods that may be employed include stationary culture, shake culture or aerobic submerged or stirred culture, for instance. For mass production, submerged aerobic culture is of course preferable. While the conditions of cultivation, of course, depend on the species or strain of microorganism, the cultural method used and so on, fermentation is generally conducted at a temperature of about 15° to 37° C. with the initial pH being set at pH about 3 to 8. Particularly desirable conditions are about 23° to 32° C. in the intermediate stage of cultivation and pH about 4 to 6 at the start of cultivation. While the cultivation time is also dependent on the above-mentioned conditions, it is desirable to continue cultivation until the titer of the physiologically active substance has reached a maximum. In the case of shake culture or submerged aerobic culture in a liquid medium, the duration of time to such maximum titer is generally about 1 to 8 days.

The FA-5859 thus elaborated occurs mostly in the liquid phase of the fermentation broth. Therefore, it is a recommended procedure to separate the broth into a supernatant and a cellular mass by filtration or centrifugation and purity the supernatant to recover the desired substance. However, it is also possible to subject the fermentation broth as such directly to a known purification procedure.

To harvest FA-5859 from the broth, the procedures generally known for the isolation of microbial metabolites can be employed.

For example, microbial cells are removed by centrifugation and the active product is separated and purified from the supernatant fluid.

Thus, such procedures as the one utilizing solubilities or a difference in solubility in various solvents, precipitation from a solution, the method utilizing differential rate of precipitation, a difference in adsorptive affinity for a given adsorbent, ion exchange chromatography on ion exchangers, concentration under reduced pressure, crystallization, recrystallization, drying, etc. can be utilized either singly or in a suitable combination or in repetition.

A typical examplary procedure is as follows. The filtrate obtained from the fermentation broth is passed through a strongly acidic cation exchange resin, e.g. Amberlite IR-120 (H+) [Rohm & Haas Co., U.S.A.], whereby FA-5859 is adsorbed on the resin. Elution of FA-5859 from the resin is carried out with aqueous ammonia, an aqueous solution of alkali, an aqueous solution of a mineral acid or of an inorganic salt (e.g. sodium chloride, ammonium chloride, sodium sulfate, ammonium sulfate). Desalting of the eluate thus obtained is carried out with an adsorbent such as activated carbon for adsorption of the active compound and with a hydrophilic organic solvent system for desorption. The hydrophilic organic solvent may for example be a mixture of water with a lower ketone such as acetone, methyl ethyl ketone, methyl isobutyl ketone, etc., or a lower alcohol such as methanol, ethanol, isopropyl alcohol, propanol, butanol, isobutyl alcohol, etc., or with a mixture of such solvents. When water-soluble high polymers are present as impurities, these impurities can be removed by the conventional molecular seive method. Thus, because FA-5859 is a low molecular weight substance, water-soluble high polymers can be adsorbed and removed by means of, for example, Sephadex G-10 [Pharmacia Fine Chemicals (Sweden)]. To purify the crude product thus obtained, the amphoteric property of FA-5859 can be utilized. Thus, column chromatography on a buffered cation exchange resin can be employed with advantage. Thus, a strongly acidic cation exchange resin, such as Amberlite IR-120, Dowex 50X2 [Dow Chemical Co., U.S.A.] or Diaion SK1A [Mitsubishi Chemical Industries, Japan], is buffered with a buffer solution at a suitable pH, e.g. pH 4, and a solution of the crude substance is passed through the resin to adsorb the active compound. Elution is carried out with a buffer solution at a higher pH than the pH of the buffer used for adsorption. The eluate is again desalted with the same strongly acidic cation exchange resin as above, elution being similarly carried out. For removal of concomitant impurities, the eluate is further passed through a column of a strongly basic anion exchange resin, e.g. Dowex 1 (OH−) [Dow Chemical Co., U.S.A.], and the effluent is concentrated under reduced pressure and lyophilized. The resultant syrup gives hygroscopic crystals of FA-5859.

FA-5859 can be converted to a pharmacologically acceptable salt by the established procedure. As examples of the acid used for this conversion to a salt, there may be mentioned hydrochloric acid, sulfuric acid, nitric acid, oxalic acid, acetic acid, succinic acid, citric acid, fumaric acid, etc.

The physico-chemical properties of FA-5859 (free form) as obtained in Example 2 which appears hereinafter are as follows.

(a) Elemental analysis (%) (after drying over phosphorus pentoxide under reduced pressure at 60° C. for 10 hours)
C: 52.48%
H: 9.04%
N: 13.25%

(b) Molecular weight: $2.4–3.3 \times 10^2$ ($H_2O$) (by VPO method)

(c) Empirical formula: $C_9H_{18}N_2O_3$ (d) Specific rotation: $[\alpha]_D^{23} - 17.4°$ (c=1, $H_2O$)

(e) Ultraviolet absorption spectrum:
No characteristic absorptions at wavelengths over 210 nm.

(f) Infrared absorption spectrum:
Principal absorptions (wave-numbers) are as follows: 3420(s), 3260(sh), 3080(m), 1660(s), 1590(s), 1485(s), 1400(s), 1325(m), 1295(m), 1145(w), 1105(w), 1060(w), 970(m), 945(m) (cm$^1$) w: weak, m: medium, s: strong, sh: shoulder
Refer to FIG. 1 (potassium bromide disk)

(g) Solubilities:
Insoluble: Petroleum ether, hexane, diethyl ether, benzene, ethyl acetate, chloroform
Hardly soluble: Pyridine, acetone, dimethyl sulfoxide, dimethylformamide
Soluble: Ethanol, methanol
Readily soluble: Water (h) Color reactions
Positive: Iodine reaction
Negative: Greig-Leaback, ninhydrin, Sakaguchi, Molisch and Ehrlich reactions (i) Basic, acidic or neutral: Amphoteric (j) Color of the substance: Colorless (k) Appearance of crystals: Colorless hygroscopic crystals (l) Nuclear magnetic resonance spectrum ($CD_3OD$, 100 MHz):

1.98(3H,s), 2.42(2H,d), 3.19(9H,s), 3.56(2H,d), 4.7(1H,m)

s: singlet, d: doublet, m: multiplet (m) Stability: Stable in aqueous solution at pH 3 to 9 under heating at 100° C. for 10 minutes.

The physico-chemical properties of FA-5859.hydrochloride as obtained in Example 3 which appears hereinafter are as follows:

(a) Elemental analysis (%): (after drying under reduced pressure over phosphorus pentoxide at 60° C. for 10 hours)
C: 45.29%
H: 8.18%
N: 11.24%
Cl: 14.36%

(b) Empirical formula: $C_9H_{18}N_2O_3 \cdot HCl$
(c) Melting point: 215° C. (decompn.)
(d) Specific rotation: $[\alpha]_D^{23} -20.5°$ (C=1, H$_2$O)
(e) Ultraviolet absorption spectrum: No characteristic absorptions at wavelengths over 210 nm.
(f) Infrared absorption spectrum:
Dominant absorptions (wave-numbers) are as follows. 3400(m), 3250(s), 3190(sh), 3045(s), 2600-2400(w), 1730(s), 1660(s), 1530(m), 1480(s), 1420(m), 1405(s), 1375(m), 1290(m), 1205(m), 1160(s), 1140(sh), 1135(s), 1040(w), 960(w), 935(m), 915(m), 865(w), 800(m), 665(m), 625(w), 600(s), 560(w) (cm$^{-1}$) (w: weak, m: medium, s: strong)
Refer to FIG. 2 (potassium bromide disc)
(g) Solubilities
Insoluble: petroleum ether, hexane, diethyl ether, benzene, ethyl acetate, chloroform
Hardly soluble: pyridine, acetone, dimethyl sulfoxide, dimethylformamide
Soluble: ethanol, methanol
Readily soluble: water
(h) Color reactions:
Positive: iodine reaction
Negative: Greig-Leaback, ninhydrin, Sakaguchi, Molisch and Ehrlich reactions
(i) Color of the substance: colorless
(j) Appearance of crystals: colorless needles
(k) Stability: Aqueous solutions at pH 3 to 9 are stable at 100° C. for 10 minutes.

The molecular formula of FA-5859 and the NMR signal at δ 3.19 ppm (9H,s) suggest the presence of a trimethylammonium group in the molecule. Moreover, the NMR spectrum indicates the presence of methyl protons of the acetyl group (CH$_3$CO—) at a 1.98 ppm (3H,s) and a couple of methylene protons (—CH$_2$—×2) at δ 2.42 ppm (2H,d) and 3.56 ppm (2H,d) and a methine proton

at δ 4.7 ppm. Decoupling studies reveal that the above couple of methylene protons are respectively coupled with the methine proton at δ 4.7 ppm, suggesting the existence of a partial structure of

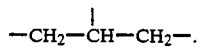

Moreover, the molecular formula of this compound suggests the presence of a carboxyl group. This is also apparent from the fact that a C=O vibration is seen at 1590 cm$^{-1}$ in the case of the free compound and at 1730 cm$^{-1}$ in the case of the hydrochloride.

Therefore, the following planar structural formula may be advanced for FA-5859.

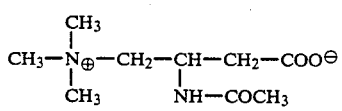

Accordingly, FA-5859 is considered to be a novel compound.

Then, the fatty acid degradation inhibiting activity of physiologically active substance FA-5859 was determined in accordance with the method described in Biochemical Society of Japan (ed.): Seikagaku Zikken Koza (Lectures on Biochemical Experiments), Vol. 9, Metabolism of Lipids, p. 75 (1975, Tokyo Kagaku Dozin, Japan) using rat liver homogenates. Thus, an SD strain rat (7 weeks of age, male) was fasted for 2 days and, then, bled to death. The liver was immediately excised and homogenized with 10 times (w/v) of a 0.25 M sucrose solution containing a 5 mM Tris-HCl buffer (pH 7.5) using a Teflon rod homogenizer. The homogenate was centrifuged at 600 xg for 20 minutes and the supernatant was further centrifuged at 30,000 xg for 30 minutes. The resultant pellets were suspended in the same sucrose solution as above to a concentration of 0.2 g wet liver weight/0.5 ml solution and 0.5 ml of the suspension was used as the enzyme solution in the reaction.

Then, 3.0 ml of a reactant mixture consisting of 30 μmole of potassium phosphate buffer (pH 7.5), 300 μmole of KCl, 3 μmole of ATP, 3 μmole of MgCl$_2$, 120 μmole of sucrose, 0.6 μmole of 1-$^{14}$C palmitic acid (0.1 μCi and bovine serum albumin with a molar ratio of 1:5, pH 7.5), 0.6 μmole of L-carnitine, 0.6 μmole of Coenzyme A, 0.2 μmole of oxalacetic acid, 0.1 ml of water or an aqueous solution containing an inhibitor and 0.5 ml of the enzyme solution was incubated aerobically at 37° C. for 20 min. in a sealed tube and the reaction was stopped by adding 0.4 ml of 70% perchloric acid. $^{14}$CO$_2$ formed was trapped on a strip of filter paper treated with Hyamine Hydroxide 10-X [Packard, Holland]. As compared with the inhibitor-free control, the inhibitory activity of FA-5859 was 17% inhibition at 250 μg/ml, 25% at 500 μg/ml and 36% at 1000 μg/ml.

The acute toxicity (LD$_{50}$) of FA-5859 in mice was ≧400 mg/kg, i.v.

FA-5859 or a salt thereof is useful as a fatty acid decomposition inhibitor, for instance.

When FA-5859 or a salt thereof is used as such a fatty acid decomposition inhibitor for the treatment of diabetes in mammalian animals (e.g. mouse, rat, man), it is administered at a daily dose of about 0.2 to 200 mg/kg as FA-5859. FA-5859 or a salt thereof can be administered orally is such dosage forms as tablets, granules, capsules, liquids, etc., or non-orally in the form of an injectable preparation.

Moreover, FA-5859 can be used as a biochemical reagent for studies on fatty acid metabolism. For example, since carnitine deficiency can be easily established by adding FA-5859 to a reaction system, the role of carnitine in fatty acid oxidation can be studied with more clarity. Moreover, since the physiological roles of mitochondria and peroxisome in fatty acid oxidation have substantially not been clarified, the role of peroxisome and the relation of peroxisome with the oxidation process in mitochondria can be studied by inhibiting the takeup of fatty acids into mitochondria by the addition of FA-5859. In these cases, the reaction system used generally for fatty acid oxidation is employed and FA-5859 is generally used in a concentration of about 0.5 mg/ml to 50 mg/ml, although the concentration should vary with the concentration of intracellular particulate components.

FA-5859 is also useful as an intermediate for the synthesis of compounds having still improved fatty acid decomposition inhibiting activity.

When FA-5859 or a salt thereof is subjected to hydrolysis, deacetyl-FA-5859 or a salt thereof is obtained.

The hydrolysis according to this invention can be effected by any method that is conductive to a cleavage of an amide bond. For example, methods employing an acid, a base or an ion exchange resin may be mentioned. Examples of said acid include inorganic acids such as sulfuric acid and hydrochloric acid and examples of said base include potassium hydroxide, sodium hydroxide and barium hydroxide. Examples of said ion exchange resin include Dowex-50 (Dow Chemical, U.S.A.), Amberlite IR-120 (Rohm and Haas Co., U.S.A.) and Diaion-SKIA and SKIB (Mitsubishi Chemical Industries Ltd., Japan).

When the acid is employed, the reaction is preferably conducted in aqueous solution and when an aqueous solvent is employed, it is preferably a mixture of water with methanol, ethanol, butanol or the like. The reaction is conducted generally at about 60° to 200° C. and preferably at about 90° to 120° C., generally for about 30 minutes to 30 hours and preferably for about 3 to 16 hours.

When the base is employed, the reaction is desirably conducted in aqueous solution. This reaction is also desirably conducted in an aqueous solvent such as a mixture of water with methanol, ethanol, butanol or the like. This reaction is carried out generally at about 60° to 200° C. and preferably at about 90 to 120° C., generally for about 30 minutes to 30 hours and preferably for about 3 to 16 hours.

When the ion exchange resin is employed, the resin is suspended in an aqueous solution of the starting material compound and the suspension is heated. This reaction is conducted generally at 60 to 200° C. and preferably at about 90° to 120° C., generally for about 30 minutes to 30 hours and preferably for about 3 to 16 hours.

Isolation of deacetyl-FA-5859 or a salt thereof from the reaction product mixture can be accomplished by the per se conventional procedures such as ion exchange, adsorption, concentration, crystallization, etc. While the desired compound can be isolated optionally as the free compound or as a salt thereof, it is more expedient to isolate it in the form of a salt.

A typical procedure for isolating the desired substance from the reaction mixture comprises adsorbing the substance on a strongly acidic ion exchange resin or the like, desorbing the same with hydrochloric acid or the like and collecting ninhydrin-positive fractions. When the hydrolysis is effected with hydrochloric acid for instance, a more expedient procedure may be adopted. Thus, the reaction mixture is concentrated under reduced pressure to remove the excess hydrochloric acid and a solvent such as methanol, ethanol or diethyl ether is added to the residue to give hydrochloride of the substance as crystals.

By the process described above is obtained deacetyl-FA-5859 as the free compound or as a salt.

The salt of deacetyl-FA-5859 or FA-5859 can also be converted to the respective free form. This can be accomplished, for example, by adsorbing the acid or base forming the salt on an ion exchange resin or the like.

The free form of deacetyl-FA-5859 is capable of forming a salt and, therefore, can be converted to a pharmacologically acceptable salt by the established procedure. As examples of the acid used to provide such a salt may be mentioned hydrochloric acid, sulfuric acid, nitric acid, oxalic acid, acetic acid, succinic acid, citric acid and fumaric acid.

Then, the fatty acid degradation inhibiting activity of deacetyl-FA-5859, a physiologically active substance, was determined using the mitochondria fraction of a rat liver homogenate in accordance with the method described in Biochemical Society of Japan (ed.): Seikagaku Zikken Koza (Lectures on Biochemical Experiments), vol. 9, Metabolism of Lipids, page 75 (1975, Tokyo Kagaku Dozin, Japan) and I.B. Fritz et al.: Proceedings of the National Academy of Sciences, U.S.A. 54, 1226, 1965. Thus, an SD strain rat (7 weeks of age, male) was fasted for 24 hours and bled to death. The liver was promptly excised and homogenized with 10 times (w/v) of a 0.25 M sucrose solution containing 5 mM of Tris-HCl buffer (pH 7.5) using a Teflon rod homogenizer. The homogenate was centrifuged at 600 xg for 20 minutes and the supernatant was further centrifuged at 30,000 xg for 30 minutes. The resultant pellets were suspended in the same sucrose solution as above to a concentration of 0.2 g wet liver weight/0.5 ml solution and 0.5 ml of the suspension was used as the enzyme solution in the reaction. Then, 2.5 ml of a reactant mixture consisting of 30 $\mu$mole of potassium phosphate buffer (pH 7.5), 300 $\mu$mole of KCl, 3 $\mu$mole of $MgCl_2$, 120 $\mu$mole of sucrose, 0.03 $\mu$mole of L-malic acid, 3 $\mu$mole of ATP, 3 $\mu$mole of L-carnitine, 0.6 $\mu$mole of Co-enzyme A, 7.5 $\mu$mole of NAD, 0.6 $\mu$mole of 1-$^{14}$C palmitic acid (0.2$\mu$ Ci and bovine serum albumin with a molar ratio of 1:5, pH 7.5), 0.1 ml of water or an aqueous solution containing an inhibitor and 0.5 ml of the enzyme solution was incubated aerobically at 37° C. for 20 min. in a sealed tube and the reaction was stopped by adding 0.4 ml of 70% perchloric acid. $^{14}CO_2$ formed was trapped on a strip of filter paper treated wiht Hyamine Hydroxide 10-X [Packerd, Holland]. The inhibitory activity of this deacetyl-FA-5859, i.e. the concentration that causes a 50% inhibition of degradation activity relative to the inhibitor-free control, was 4 to 8 $\mu$g/ml.

The acute toxicity $LD_{50}$ of deacetyl-FA-5859 in mice was not less than 400 mg/kg by intravenous administration.

Deacetyl-FA-5859 or a salt thereof in accordance with this invention is useful as a fatty acid degradation inhibitor.

To use deacetyl-FA-5859 or a salt thereof as a fatty acid degradation inhibitor for the treatment of diabetes in mammalian animals (e.g. mouse, rat, man), for instance, it is administered in a daily dose of about 0.2 to 200 mg/kg as deacetyl-FA-5859.

Deacetyl-FA-5859 or a salt thereof can be administered in the conventional manner, e.g. orally in such dosage forms as tablets, granules, capsules, liquids, etc. or non-orally in the form of a injection, for instance.

Deacetyl-FA-5859 according to this invention can be used also as a biochemical reagent for studies on fatty acid metabolism. By way of illustration, since carnitine deficiency can be easily established by adding deacetyl-FA-5859 to a reaction system, the role of carnitine in fatty acid oxidation can be clarified in detail. Moreover, because the physiological roles of mitochondria and peroxisome in fatty acid oxidation have substantially not clarified the role of peroxisome and the relation of peroxisome with the oxidation process in mitochondria could be studied by inhibiting the takeup of fatty acids into mitochondria by addition of deacetyl-FA-5859. In these cases, the reaction system used generally for fatty acid oxidation is employed and deacetyl-FA-5859 is generally used advantageously in a concentration of about 0.1 μg/ml to 1000 μg/ml, although the preferred concentration depends on the concentration of intracellular particulate components.

Moreover, deacetyl-FA-5859 according to this invention is also useful as an intermediate for the synthesis of compounds having improved fatty acid decomposition inhibiting activity.

When the compound [1] is produced by subjecting the compound [2] to elimination reaction of the protective group, a conventional manner employed in the peptide synthesis such as hydrolysis, catalytic reduction, acid treatment may be employed. The hydrolysis can be effected by any method that is conducive to a cleavage of an amide bond. For example, methods employing an acid, a base or an ion exchange resin may be mentioned. Examples of said acid include inorganic acids such as sulfuric acid and hydrochloric acid and examples of said base include potassium hydroxide, sodium hydroxide and barium hydroxide. Examples of said ion exchange resin include Dowex-50 (Dow Chemical, U.S.A.), Amberlite IR-120 (Rohm and Haas Co., U.S.A.) and Diaion-SKIA and SKIB (Mitsubishi Chemical Industries Ltd., Japan).

When the acid is employed, the reaction is preferably conducted in aqueous solution and when an aqueous solvent is employed, it is preferably a mixture of water with methanol, ethanol, butanol or the like. The reaction is conducted generally at about 60° to 200° C. and preferably at about 90° to 120° C., generally for about 30 minutes to 30 hours and preferably for about 3 to 16 hours.

When the base is employed, the reaction is desirably conducted in aqueous solution. This reaction is also desirably conducted in an aqueous solvent such as a mixture of water with methanol, ethanol, butanol or the like. This reaction is carried out generally at about 60° to 200° C. and preferably at about 90° to 120° C., generally for about 30 minutes to 30 hours and preferably for about 3 to 16 hours.

When the ion exchange resin is employed, the resin is suspended in an aqueous solution of the starting material compound and the suspension is heated. This reaction is conducted generally at 60 to 200° C. and preferably at about 90° to 120° C., generally for about 30 minutes to 30 hours and preferably for about 3 to 16 hours.

Said catalytic reduction is carried out in an alcohol such as methanol or ethanol or a mixed solvent composed of water and an alcohol, in the presence of a catalyst such as palladium black or palladium-on-carbon introducing hydrogen gas into the reaction system, if necessary under pressure. The reaction is carried out at 0° C. to 50° C., preferably at 20° to 30° C., and the reaction time is within about 0.5 to 5 hours, preferably within about 1 to 3 hours.

The acid to be used in said acid treatment is, for example, hydrogen bromide-acetic acid, hydrochloric acid-acetic acid, hydrochloric acid-dioxane, trifluoroacetic acid, methanesulfonic acid or trifluoromethanesulfonic acid. The temperature of the acid treatment should advisably be selected depending upon the acid used within the range of about −10° C. and 50° C., preferably about 0° C. to 25° C., and the reaction time within the range of about 30 minutes to 24 hours.

The acetylation of the compound resulting from the elimination reaction of protective group from a compound [2] or a salt thereof is effected by reacting said compound with acetic anhydride, or a mixed acid anhydride prepared by reacting acetic acid with an alkoxycarbonyl chloride such as methyl chlorocarbonate, ethyl chlorocarbonate, butyl chlorocarbonate, propyl chlorocarbonate or isobutyl chlorocarbonate, in water or a mixed solvent composed of water and an organic solvent such as acetone, dioxane, acetonitrile, dimethylformamide or tetrahydrofuran. The reaction may be conducted in the presence of a deacidifying agent such as an organic base (e.g. pyridine, triethylamine, trimethylamine) or a hydroxide, oxide or bicarbonate of an alkali or alkaline earth metal (e.g. sodium, potassium, calcium). The reaction temperature is about −10° C. to 50° C., preferably about 0° C. to 25° C.

The trimethylation of compound [3] or a salt thereof in accordance with the present invention is carried out, for example, by reacting compound [3] or a salt thereof with dimethyl sulfate, methyl bromide, methyl chloride or methyl iodide in water or a mixture of water and an organic solvent such as acetonitrile, dioxane, tetrahydrofuran or dimethylformamide. The reaction may be performed in the presence of, for instance, a hydroxide or oxide of an alkali or alkaline earth metal such as sodium, potassium or calcium, as necessary. The reaction temperature is about −10° C. to 50° C., preferably about 0° C. to 20° C.

The desired products yielded by either of the above reactions can be isolated and purified by conventional separation/purification techniques, such as chromatography, recrystallization, etc.

The hydrolysis reaction, which may be conducted after the trimethylation of the compound [3] or its salts, can be effected by any method that is conductive to a cleavage of an amide bond. For example, methods employing an acid, a base or an ion exchange resin may be mentioned. Examples of said acid include inorganic acids such as sulfuric acid and hydrochloric acid and examples of said base include potassium hydroxide, sodium hydroxide and barium hydroxide. Examples of said ion exchange resin include Dowex-50 (Dow Chemical, U.S.A.), Amberlite IR-120 (Rohm and Haas Co., U.S.A.) and Diaion-SKIA and SKIB (Mitsubishi Chemical Industries Ltd., Japan).

When the acid is employed, the reaction is preferably conducted in aqueous solution and when an aqueous solvent is employed, it is preferably a mixture of water with methanol, ethanol, butanol or the like. The reaction is conducted generally at about 60 to 200° C. and preferably at about 90° to 120° C., generally for about 30 minutes to 30 hours and preferably for about 3 to 16 hours.

When the base is employed, the reaction is desirably conducted in aqueous solution. This reaction is also desirably conducted in an aqueous solvent such as a mixture of water with methanol, ethanol, butanol or the like. This reaction is carried out generally at about 60 to 200° C. and preferably at about 90° to 120° C., generally for about 30 minutes to 30 hours and preferably for about 3 to 16 hours.

When the ion exchange resin is employed, the resin is suspended in an aqueous solution of the starting material compound and the suspension is heated. This reaction is conducted generally at 60° to 200° C. and preferably at about 90° to 120° C., generally for about 30 minutes to 30 hours and preferably for about 3 to 16 hours.

The compound [2], which is employed as the starting compound in the method of the present invention, can be produced for example by the following procedure:

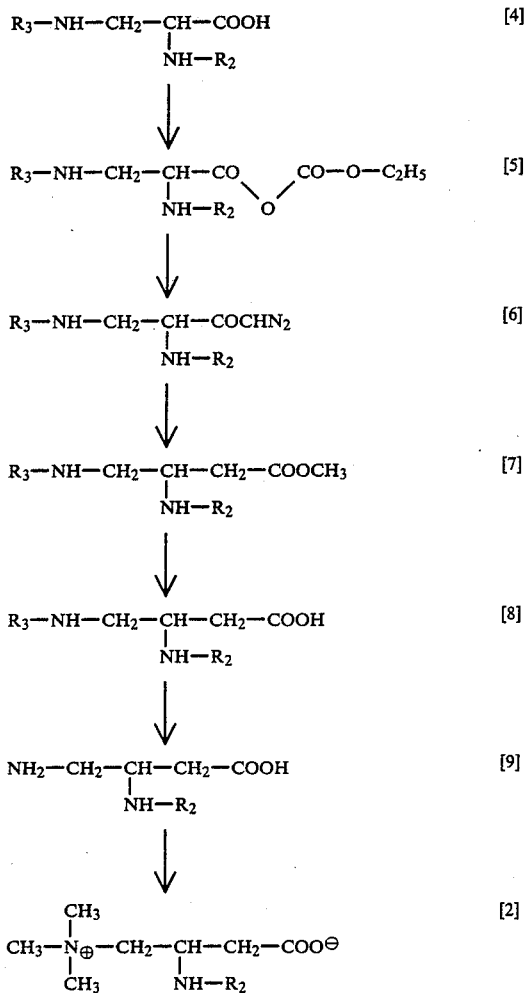

The compound [4] may be produced by for example a method described in Synthesis page 266, 1981 or a similar method thereof.

The compound [3], which is the starting compound of the present method, can be produced by for example the following procedure.

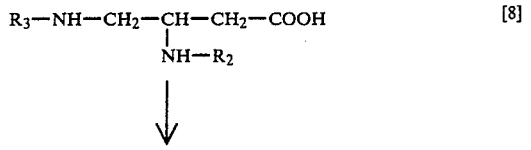

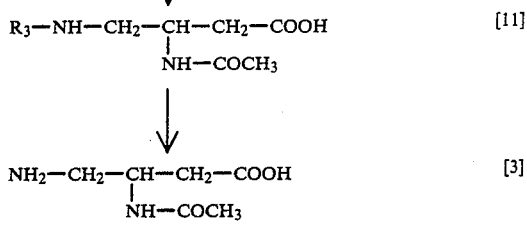

In the above formulas, $R_2$ has the same meaning as mentioned above. $R_3$ is a protective group which is eliminable under conditions different from those for eliminating the protective group $R_2$. Examples of such protective group $R_3$ are benzyloxycarbonyl, tert-butoxycarbonyl, p-nitrobenzyloxycarbonyl, p-methoxybenzyloxycarbonyl, trityl, tosyl, tert-amyloxycarbonyl, isobornyloxycarbonyl, diphenylphosphinyl, o-nitrophenylsulfenyl and phthalyl.

The compound [5] is produced from the compound [4], for example, by reacting the compound [4] with an acid chloride such as ethyl chlorocarbonate, methyl chlorocarbonate, propyl chlorocarbonate, butyl chlorocarbonate or isobutyl chlorocarbonate, in an organic solvent such as ethyl acetate, methyl acetate, dioxane, tetrahydrofuran or acetonitrile. The reaction may be carried out in the presence of an organic base such as N-methylmorpholine, N-ethylmorpholine, triethylamine, trimethylamine or pyridine. The reaction temperature is about $-20°$ C. to 30° C., preferably about $-10°$ C. to 0° C.

The compound [6] is produced by reacting the compound [5] with diazomethane. Thus, for example, the compound [5] is reacted with diazomethane in an organic solvent such as ethyl acetate, methyl acetate, tetrahydrofuran, dioxane, acetonitrile or diethyl ether, at a temperature of about $-20°$ C. to 30° C., preferably about $-10°$ C. to 25° C., for about an hour to 24 hours. Diazomethane may either be blown into the solution of the compound [5] or be added to the solution of the compound [5] as a saturated solution of diazomethane in an organic solvent such as diethyl ether or ethyl acetate.

The compound [7] are produced from the compound [6], for example by reacting the compound [6] in a methanol solution with a silver salt of benzoic acid or acetic acid, for instance, dissolved in an organic base such as trimethylamine, triethylamine, N-methylmorpholine, N-ethylmorpholine or pyridine, at about $-5°$ C. to 50° C., preferably about 0° C. to 27° C., in the dark, for about 30 minutes to 10 hours.

The compound [8] is produced by saponifying the compound [7]. Said saponification is carried out by contacting the compound [7] with a hydroxide of sodium, potassium or barium, for instance, in water, an organic solvent such as methanol, ethanol, dioxane, tetrahydrofuran or acetonitrile, or a mixed solvent composed of water and an organic solvent such as mentioned above, at about $-10°$ C. to 50° C., preferably about 0° C. to 27° C., for about an hour to 5 hours.

The compound [9] is produced from the compound [8] by selective elimination of $R_3$. Said elimination can be performed by a method conventionally used in the peptide syntheses, namely in the manner as mentioned above for the protective group elimination from the compound [2].

The compound [2] can be produced by subjecting the compound [9] to trimethylation. Said trimethylation can be carried out in the manner as mentioned above for the trimethylation of the compound [3].

Conversion of the compound [8] to the compound [10] can be effected in the manner as mentioned above for the protective group elimination from the compound [2].

The compound [11] can be produced by acetylation of the compound [10]. Said acetylation can be performed in the manner as mentioned above for the acetylation step in the process comprising protective group elimination from the compound [2] followed by optional acetylation.

The compound [3] can be produced by subjecting the compound [11] to elimination reaction of protective group. Said elimination reaction of protective group can be conducted in the manner as mentioned above for the production of the compound [9] from the compound [8].

Each product in each of the above-mentioned reactions can be isolated and purified by conventional separation/purification methods, such as chromatography, recrystallization, etc.

As is evident from the above description, the compound [8] can be used as intermediates in the synthetic production of useful compounds.

In each of the above-mentioned reaction steps, each compound may be used in the form of a salt. Such salt includes, among others, salts with sodium, potassium, calcium, barium, triethylamine, pyridine, hydrogen chloride, hydrogen bromide or hydrogen iodide.

Figure 2:
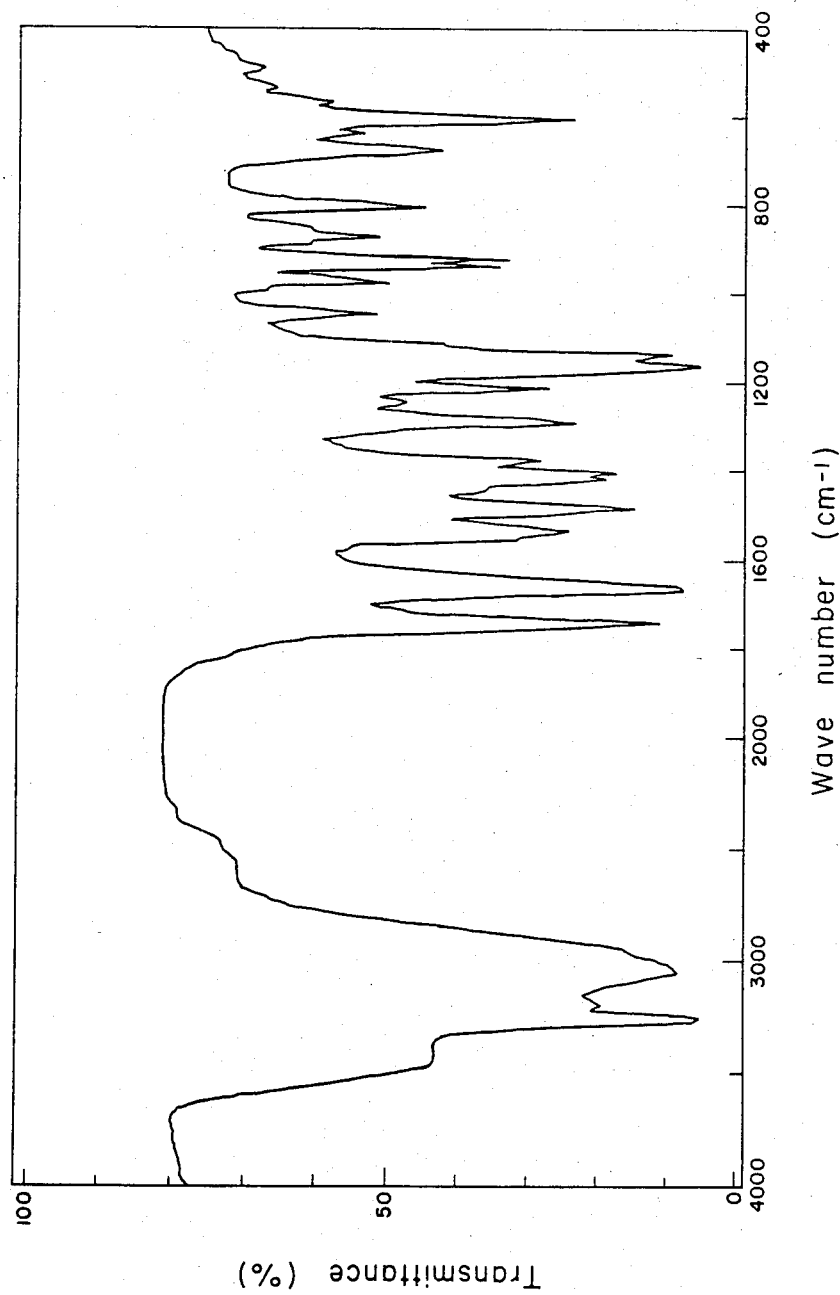

FIG. 1 is an infrared absorption spectrum of phisiologically active substance FA-5859 as obtained in Example 2, and FIG. 2 is an infrared absorption spectrum of the hydrochloride of physiologically active substance FA-5859 as obtained in Example 3.

The following working examples and reference examples are further illustrative of this invention. In the examples, percent figures with respect to medium compositions are on a weight/volume basis.

EXAMPLE 1

A loopful of *Emericella quadrilineata* IFO 5859 grown sufficiently to sporulate on a potato-sucrose-agar slant was used to inoculate a 2-liter Sakaguchi flask containing 500 ml of a sterilized medium composed of 2.0% glucose, 3.0% maltose, 1.5% raw soybean flour, 1.0% corn steep liquor, 0.5% polypeptone, 0.3% yeast extract and 0.3% sodium chloride (pH 6.0), and was incubated on a reciprocating shaker at 28° C. for 2 days. Then, 1.5 l of this seed culture was added to 100 l of a fermentation medium composed of 3.0% oleic acid, 0.5% raw soybean flour, 0.5% malt extract, 0.5% polypeptone, 0.2% yeast extract, 0.1% $KH_2PO_4$, 0.05% $FeSO_4.7H_2O$, 0.05% $MnSO_4.nH_2O$ and 0.05% $MgSO_4.7H_2O$ (pH 4.5) in a 200-l fermentation tank. This fermentation was conducted at 28° C., 100 l/min. aeration, 200 r.p.m. agitation and an internal pressure of 1.0 kg/cm$^2$ for 114 hours. A couple of batches of fermentation thus obtained were pooled and the cells were removed by filtration to give a filtrate containing FA-5859.

EXAMPLE 2

A 125 l portion of the filtrate obtained in Example 1 was passed through a column of Amberlite IR-120 (H+ form) (20 l) and after the column was rinsed with 40 l of water, elution was carried out with 1N-aqueous ammonia. The eluate was concentrated under reduced pressure to a volume of 30 l to remove the ammonia and the concentrate was passed through a column of chromatographic grade activated carbon (30 l). The column was rinsed with 60 l of water and elution was carried out with 90 l of 50% aqueous methanol. The eluate was collected in 10 l fractions and the active fractions No. 5 to No. 6 were combined and concentrated under reduced pressure to give 25.5 g of a crude syrup. This crude product was dissolved in 100 ml of acetate buffer (pH 4.0) (0.05M) and the solution was passed through a column of Dowex 50×2 (500 ml) buffered with acetate buffer (0.1M) (pH 4.0). Then, elution was performed with the same buffer as above in the order of 1 l at pH 4.0, 1.5 l at pH 4.3, 1.5 l at pH 4.6 and 1.5 l at pH 5.0. The eluate was collected in 100 ml fractions and the fractions No. 32 to No. 63 were pooled and passed through a column of Amberlite IR-120 H+form) (300 ml). After the column was rinsed with 600 ml of water, elution was carried out with 1.5 l of 0.5N-aqueous ammonia. The eluate was concentrated under reduced pressure to a volume of 500 ml and the concentrate was passed through a column of Dowex 1×2 (OH$^-$ form) (200 ml), followed by washing with 200 ml of water. The effluent and washings were combined and concentrated under reduced pressure and lyophilized. Allowing the syrup to stand at room temperature yielded 10.7 g of colorless hygroscopic crystals of FA-5859 (free form). The infrared absorption spectrum of this product is reproduced in FIG. 1.

EXAMPLE 3

In 10 ml of water was dissolved 210 mg of FA-5859 free form produced in Example 2, and under ice-cooling, 1 ml of 1N-HCl was added. The mixture was concentrated under reduced pressure and after addition of 10 ml of ethanol, allowed to stand at room temperature. The resultant crystals were recrystallized from water-ethanol to give 225 mg of hydrochloride of FA-5859 as colorless needles. m.p. 215° C. (decompn.). The infrared absorption spectrum of this compound is shown in FIG. 2.

EXAMPLE 4

The following microorganisms were employed in the process described in Example 1. The results indicated that FA-5859 was invariably produced.

*Emericella quadrilineata* IFO 30911, *Emericella quadrilineata* IFO 30912, *Emericella quadrilineata* IFO 30850, *Emericella quadrilineata* IFO 30851, *Emericella nidulans* var. *acristata* IFO 30063, *Emericella nidulans* var. *acristata* IFO 30844, *Emericella cleistominuta* IFO 30839, *Emericella nidulans* var. *nidulans* IFO 30872, *Emericella nidulans* var. *lata* IFO 30847, *Emericella rugulosa* IFO 8626, *Emericella rugulosa* IFO 8629, *Emericella rugulosa* IFO 30913, *Emericella rugulosa* IFO 30852, *Emericella rugulosa* IFO 30853, *Emericella nidulans* IFO 5719, *Emericella nidulans* IFO 7077, *Emericella nidulans* IFO 30062, *Emericella sublata* IFO 30906.

EXAMPLE 5

Aspergillus sp. No. 3704 (IFO 31171, FERM BP-185) was used to inoculate a 2-liter Sakaguchi flask containing 500 ml of a sterilized seed culture medium similar to that used in Example 1. The inoculated flask was incubated on a reciprocating shaker at 28° C. for 2 days. Then, 1.5 l of this seed culture was added to 100 l of a fermentation medium composed of 3.0% soybean oil, 0.5% raw soybean flour, 0.5% malt extract, 0.5% polypeptone, 0.2% yeast extract, 0.1% $KH_2PO_4$, 0.05% $FeSO_4 \cdot 7H_2O$, 0.05% $MnSO_4 \cdot nH_2O$ and 0.05% $MgSO_4 \cdot 7H_2O$ (pH 4.5) in a 200-liter fermentation tank. This fermentation reaction was conducted at 28° C., 100 l/min. aeration, 200 r.p.m. agitation and an internal pressure of 1.0 kg/cm² for 114 hours. The cells were removed from the broth by filtration to give 80 l of a filtrate containing FA-5859.

EXAMPLE 6

The filtrate obtained in Example 5 (80 l was treated and purified in the manner as Example 2 to give 3.15 g of a syrup. This free FA-5859 syrup (3.15 g) was dissolved in 150 ml of water and under ice-cooling, 15 ml of 1N-hydrochloric acid was added. The mixture was concentrated under reduced pressure and after addition of 150 ml of ethanol, the concentrate was allowed to stand. The resultant crystals were recrystallized from ethanol to give 3.3 g of FA-5859.hydrochloride as colorless needles. m.p. 214° C. (decompn.). Elemental analysis: C, 45.39; H, 7.73; N, 11.50; Cl, 14.77%.

EXAMPLE 7

In 40 ml of constant boiling point hydrochloric acid was dissolved 1.60 g of free FA-5859 and the solution was allowed to stand at 95° C. for 16 hours. The reaction mixture was concentrated under reduced pressure and the residue was diluted with a small amount of water and concentrated under reduced pressure for a second time. To the residue was added a mixture of methanol and diethyl ether and the resultant crystals were collected by filtration. Recrystallization from methanol gave 1.20 g of deacetyl-FA-5859.2HCl. m.p. 219°–220° C.; $[\alpha]_D^{22} +6.3°$ (c=1.0, 1N -AcOH).

Elemental analysis: $C_7H_{18}O_2N_2Cl_2$. Calcd.: C, 36.05; H, 7.77; N, 12.01; Cl, 30.40(%). Found : C, 36.09; H, 7.72; N, 11.81; Cl, 29.80(%). Absorption spectrum: No characteristic absorption over the ultraviolet and visible region from 210 nm to 700 nm.

REFERENCE EXAMPLE 1

(1) (L)-α-Benzyloxycarbonylamino-β-tert-butoxycarbonylaminopropionic acid (6.1 g) was dissolved in 100 ml of ethyl acetate, the solution was cooled to −10° C., 1.8 g of N-methylmorpholine and 1.9 g of ethyl chlorocarbonate were added thereto, and the mixture was stirred at −10° C. for one hour. The insoluble matter was filtered off, a diethyl ether solution containing a large excess of diazomethane was added to the filtrate, and the mixture was stirred at 0° C. for one hour and then at room temperature for 12 hours. The solvent was distilled off under reduced pressure, the residue was dissolved in 50 ml of methanol, a solution of 200 mg of silver benzoate in 2 ml of triethylamine was added to the solution, and the mixture was stirred in the dark place at room temperature for 4 hours. The insoluble matter was filtered off, the filtrate was concentrated under reduced pressure, and the residue was dissolved in 100 ml of ethyl acetate. The ethyl acetate solution was washed in sequence with 10% aqueous citric acid, 5% sodium hydrogen carbonate and water, and dried over anhydrous sodium sulfate. Upon distilling off the ethyl acetate, methyl (L)-β-benzyloxycarbonylamino-γ-tert-butoxycarbonylaminobutyrate was crystallized out. The crystals were recrystallized from ethyl acetate-petroleum ether. Yield 4.8 g (73%).

Melting point: 100°–101° C.

$[\alpha]_D^{24} +6.0°$ (C=1, in dimethylformamide)

Elemental analysis: $C_{18}H_{26}O_6N_2$. Calcd.: C, 59.00; H, 7.15; N, 7.65 (%). Found : C, 59.30; H, 7.07; N, 7.74 (%).

(2) 3.60 g of methyl (L)-β-benzyloxycarbonylamino-γ-tert-butoxycarbonylaminobutyrate obtained by the above procedure was dissolved in 20 ml of methanol, and 12 ml of 1N sodium hydroxide was added at 0° C. The mixture was stirred at room temperature for 3 hours and then neutralized with citric acid, and 100 ml of ethyl acetate was added. The ethyl acetate solution was washed with water, dried over anhydrous sodium sulfate and concentrated under reduced pressure. The crystalline precipitate was collected by filtration and recrystallized from ethyl acetate to give crystals of (L)-β-benzyloxycarbonylamino-γ-tert-butoxycarbonylaminobutyric acid. Yield 2.96 g (85%).

Melting point: 136°–137° C.

$[\alpha]_D^{24} +12.2°$ (C=1, in dimethylformamide)

Elemental analysis: $C_{17}H_{24}O_6N_2$. Calcd.: C, 57.94; H, 6.87; N, 7.95 (%). Found : C, 57.97; H, 6.76; N, 8.13 (%).

REFERENCE EXAMPLE 2

0.75 g of (L)-β-benzyloxycarbonylamino-γ-tert-butoxycarbonylaminobutyric acid obtained in Reference Example 1 was dissolved in 10 ml of trifluoroacetic acid, and the solution was allowed to stand at room temperature for 10 minutes. The liquid reaction mixture was evaporated to dryness under reduced pressure, and the residue was further dried under reduced pressure. This was dissolved in 7 ml of 10% sodium hydroxide, the solution was cooled to 0° C., 0.65 ml of dimethyl sulfate was added thereto, and the mixture was stirred at room temperature for an hour. The liquid reaction mixture was subjected to Amberlite IR-120 (H+ form) column chromatography. The column was washed with water and eluted with 1N liqueous ammonia. Eluate fractions from 150 ml to 220 ml were pooled and concentrated under reduced pressure. Drying of the residue under reduced pressure gave 0.44 g of (L)-β-benzyloxycarbonylamino-γ-trimethylaminobutyric acid as a viscous oil.

Thin layer chromatography (carrier: silica gel 60 $F_{254}$, Merck, West Germany):

(1) Rf=0.13 (n-propanol:water=4:1)

(2) Rf=0.26 (n-propanol:water:15N-aqueous ammonia)=70:28:2

REFERENCE EXAMPLE 3

(1) (L)-β-Benzyloxycarbonylamino-γ-tert-butoxycarbonylaminobutyric acid (1.4 g) obtained in Reference Example 1 was dissolved in 30 ml of 80% aqueous methanol, and catalytic hydrogenation was performed in the presence of palladium black. The catalyst was filtered off, the methanol was distilled off, and the residue was dissolved by adding 10 ml of water thereto together with 840 mg of sodium hydrogen carbonate. To this solution, there were added at 0° C. 10 ml of acetonitrile and 0.5 ml of acetic anhydride. The resulting mixture was stirred at 0° C. for an hour and at room temperature for 12 hours. The acetonitrile was distilled off, the residue was washed with 50 ml of diethyl ether added thereto, and the aqueous layer was neutralized with 0.1N hydrochloric acid and extracted with three 50-ml portinos of ethyl acetate. The ethyl acetate layers were combined and dried over anhydrous sodium sulfate. The ethyl acetate was distilled off, and the residue was crystallized with petroleum benzine and recrystallized from ethyl acetate to give crystals of (L)-$\beta$-acetylamino-$\gamma$-tert-butoxycarbonylaminobutyric acid. Yield 0.88 g (86%).

Melting point: 140°–141° C.

$[\alpha]_D^{24} + 26.0°$ (c=0.9, in dimethylformamide)

Elemental analysis: $C_{11}H_{20}O_5N_2$. Calcd.: C, 50.75; H, 7.75; N, 10.76 (%). Found : C, 50.53; H, 7.35; N, 10.68 (%).

(2) (L)-$\alpha$-Acetylamino-$\gamma$-tert-butoxycarbonylaminobutyric acid (700 mg) obtained by the above procedure was dissolved in 10 ml of trifluoroacetic acid, and the solution was allowed to stand at room temperature for 30 minutes. The trifluoroacetic acid was then distilled off, and the residue was dried under reduced pressure and dissolved in 100 ml of water. The solution was passed through a Dowex 50×2 (H+ form, 300 ml ) column. The column was washed with water and eluted with 0.5N ammonia. The eluate was concentrated under reduced pressure and the crystalline precipitate was collected by filtration and recrystallized from methanol to give crystals of (L)-$\beta$-acetylamino-$\gamma$-aminobutyric acid. Yield 348 mg.

Melting point: 177°–178° C. (decomposition)

$[\alpha]_D^{24} - 15.4°$ (c=0.7, in 0.1N hydrochloric acid)

Elemental analysis: $C_6H_{12}O_3N_2$. Calcd.: C, 44.99; H, 7.55; N, 17.49 (%). Found : C, 44.83; H, 7.62; N, 17.22 (%).

EXAMPLE 8

(1) 0.39 g of (L)-$\beta$-benzyloxycarbonylamino-$\gamma$-trimethylaminobutyric acid obtained in Reference Example 2 was dissolved in 5 ml of 5.7N hydrochloric acid, and the solution was heated at 90° C. for 30 minutes. The liquid reaction mixture was concentrated under reduced pressure, a small amount of water was added to the residue, and the mixture was again concentrated under reduced pressure. A mixed solvent composed of methanol and diethyl ether was added to the residue, and the resultig crystalline precipitate was collected by filtration. Thus was obtained 228 mg of (L)-$\gamma$-trimethylamino-$\beta$-aminobutyric acid (deacetyl-FA-5859).

Melting point: 219°–220° C. (decomposition)

$[\alpha]_D^{24} + 6.7°$ (c=1, in 1N acetic acid)

Elemental analysis: $C_7H_{18}O_2N_2Cl_2$. Calcd.: C, 36.05; H, 7.77; N, 12.01; Cl, 30.40 (%). Found : C, 35.96; H, 7.58; N, 11.88; Cl, 30.13 (%).

(2) Deacetyl-FA-5859 dihydrochloride (699 mg) obtained in Example 7 was dissolved in 20 ml of water, and thereto was added with stirring at 0° C. a solution of 1.1 g of sodium hydrogen carbonate and 0.45 ml of acetic anhydride in 10 ml of acetonitrile. The mixture was stirred at 0° C. for an hour and then at room temperature overnight. The acetonitrile was then distilled off and the residue was passed through a Dowex 50×2 (H+ form, 80 ml) column. The column was washed with 300 ml of water and eluted with 0.5N ammonia. The 220 ml–240 ml eluate fractions were pooled and concentrated under reduced pressure, and the residue was dissolved in 50 ml of water and lyophilized. The thus-obtained viscous substance was dissolved in 2.8 ml of 1N hydrochloric acid and the solution was evaporated to dryness under reduced pressure. The residue was crystallized from methanoldiethyl ether. There were obtained crystals of (L)-$\gamma$-trimethylamino-$\beta$-acetylaminobutyric acid.hydrochloride (FA-5859.hydrochloride). Yield: 510 mg.

Melting point: 222°–223° C. (decomposition)

$[\alpha]_D^{24} - 20.0°$ (c=0.75, in water)

Elemental analysis: $C_9H_{19}O_3N_2Cl$. Calcd.: C, 45.28; H, 8.02; N, 11.73; Cl, 14.85 (%). Found : C, 45.13; H, 8.24; N, 11.79; Cl, 14.73 (%).

EXAMPLE 9

(1) (L)-$\beta$-Acetylamino-$\gamma$-aminobutyric acid (288 mg) obtained in Reference Example 3 was dissolved in 8 ml of 10% sodium hydroxide. The solution was cooled to 0° C., 0.8 ml of dimethyl sulfate was added thereto, the mixture was stirred at 0° C. for 30 minutes and then at room temperature for 30 minutes and subjected to Dowex 50×2 (H+ form, 80 ml) column chromatography. The column was washed with water and eluted with 0.5N aqueous ammonia. The 205 ml–240 ml eluate fractions were pooled and concentrated under reduced pressure. The residue was dissolved in 1.5 ml of 1N hydrochloric acid and the solution was again evaporated to dryness. The residue was crystallized from methanol-diethyl ether to give crystals of (L)-$\gamma$-trimethylamino-$\beta$-acetylaminobutyric acid.hydrochloride (FA-5859 hydrochloride). Yield: 220 mg.

Melting point: 217°–218° C. (decomposition)

$[\alpha]_D^{24} - 20.2°$ (c=0.96, in water)

Elemental analysis: $C_9H_{19}O_3N_2Cl$. Calcd.: C, 45.28; H, 8.02; N, 11.73; Cl, 14.85 (%). Found : C, 44.97; H, 8.02; N, 11.49; Cl, 14.84 (%).

(2) (L)-$\gamma$-Trimethylamino-$\beta$-acetylaminobutyric acid. hydrochloride (FA-5859 hydrochloride) (100 mg) obtained by the above procedure was dissolved in 5 ml of 5.7N hydrochloric acid, and the solution was treated at 100° C. for 6 hours. The reaction mixture was concentrated under reduced pressure, a small amount of water was added to the residue and the mixture was again concentrated under reduced pressure. A mixed solvent composed of methanol and diethyl ether was added to the residue, and the resulting crystalline precipitate was collected by filtration to give 95 mg of (L)-$\gamma$-trimethylamino-$\beta$-aminobutyric acid.dihydrochloride (deacetyl-FA-5859.dihydrochloride) as crystals.

Melting point: 218°–219° C. (decomposition)

$[\alpha]_D^{24} + 6.3°$ (c=1 in 1N acetic acid)

Elemental analysis: $C_7H_{18}O_2N_2Cl_2$. Calcd.: C, 36.05; H, 7.77; N, 12.01; Cl, 30.40 (%). Found: C, 36.12; H, 7.88; N, 11.85; Cl, 30.11 (%).

EXAMPLE 10

Tablets are prepared by a conventional method employing the following ingredients:

| | |
|---|---|
| FA-5859 prepared in Example 3 | 300 mg |
| Corn starch | 50 mg |
| Lactose | 28 mg |
| Hydroxypropylcellulose-L | 20 mg |
| Magnesium stearate | 2 mg |
| | 400 mg |
| | (per tablet) |

The daily dose of the above tablets for human adults is generally 4 to 8 tablets after each meal (3 times a day).

EXAMPLE 11

Tablets are prepared by a conventional method employing the following ingredients:

| | |
|---|---|
| Deacetyl-FA-5859 prepared in Example 7 | 300 mg |
| Corn starch | 50 mg |
| Lactose | 28 mg |
| Hydroxypropylcellulose-L | 20 mg |
| Magnesium stearate | 2 mg |
| | 400 mg (per tablet) |

The daily dose of the above tablets for human is generally 2 to 4 tablets after each meal (3 times a day).

What we claim is:

1. A compound of the formula:

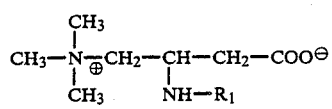

wherein $R_1$ is a hydrogen atom or an acetyl group, or a pharmacologically acceptable salt thereof.

2. A compound as claimed in claim 1, wherein $R_1$ is a hydrogen atom.

3. A compound as claimed in claim 1, wherein $R_1$ is an acetyl group.

4. An antidiabetic agent which contains an antidiabetically effective amount of the formula

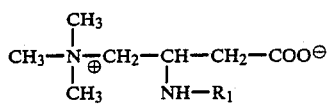

wherein $R_1$ is a hydrogen atom or an acetyl group, or a pharmacologically acceptable salt thereof, and conventional carrier.

* * * * *